(12) United States Patent
Gylleby et al.

(10) Patent No.: US 11,721,422 B2
(45) Date of Patent: Aug. 8, 2023

(54) DEVICE FOR MONITORING MEDICAMENT DELIVERY DEVICES

(71) Applicant: SHL MEDICAL AG, Zug (CH)

(72) Inventors: Stefan Gylleby, Stockholm (SE); Nikolaj Hautaviita, Bro (SE); Daniel Säll, Segeltorp (SE); Rasmus Renstad, Stockholm (SE)

(73) Assignee: SHL MEDICAL AG, Zug (CH)

( * ) Notice: Subject to any disclaimer, the term of this patent is extended or adjusted under 35 U.S.C. 154(b) by 0 days.

(21) Appl. No.: 17/158,864

(22) Filed: Jan. 26, 2021

(65) Prior Publication Data

US 2021/0158926 A1 May 27, 2021

Related U.S. Application Data

(63) Continuation of application No. 15/577,659, filed as application No. PCT/EP2016/062976 on Jun. 8, 2016, now Pat. No. 10,943,685.

(30) Foreign Application Priority Data

Jun. 12, 2015 (EP) ..................................... 15171973

(51) Int. Cl.
| | |
|---|---|
| *G16H 20/17* | (2018.01) |
| *A61M 5/32* | (2006.01) |
| *A61B 90/98* | (2016.01) |
| *A61B 50/30* | (2016.01) |
| *A61B 50/24* | (2016.01) |

(Continued)

(52) U.S. Cl.
CPC ............. *G16H 20/17* (2018.01); *A61B 50/24* (2016.02); *A61B 50/30* (2016.02); *A61B 50/36* (2016.02);

(Continued)

(58) Field of Classification Search
CPC ........ G16H 20/17; G16H 20/10; A61B 50/24; A61B 50/30

(Continued)

(56) References Cited

U.S. PATENT DOCUMENTS 5,791,471 A * 8/1998 Radmand ............ A61M 5/3213
220/908
6,283,909 B1 * 9/2001 Sharp ................... A61B 50/362
206/366

(Continued)

FOREIGN PATENT DOCUMENTS

| EP | 2287091 A1 | 2/2011 |
| TW | 200724073 A | 7/2007 |

(Continued)

OTHER PUBLICATIONS

International Search Report for Int. App. No. PCT/EP2016/062976, dated Sep. 28, 2016.

*Primary Examiner* — Ahshik Kim
(74) *Attorney, Agent, or Firm* — McDonnell Boehnen Hulbert & Berghoff LLP (57) ABSTRACT

The present disclosure relates to a device for handling medicament delivery devices and is to be used with a safety container, where the medicament delivery devices have information retaining elements having information that is unique to specific medicament delivery devices, and which medicament delivery devices are to be put in a safety container after use. The disclosed device has an information obtaining mechanism operably arranged to obtain information from the medicament delivery devices placed into the safety container.

20 Claims, 4 Drawing Sheets

(51) Int. Cl.
*G16H 20/13* (2018.01)
*G16H 40/67* (2018.01)
*A61B 50/36* (2016.01)
*G16H 20/10* (2018.01)
*A61B 17/00* (2006.01)

(52) U.S. Cl.
CPC ........... *A61B 90/98* (2016.02); *A61M 5/3205* (2013.01); *G16H 20/10* (2018.01); *G16H 20/13* (2018.01); *G16H 40/67* (2018.01); *A61B 2017/00221* (2013.01); *A61M 2205/52* (2013.01); *A61M 2205/6054* (2013.01)

(58) Field of Classification Search
USPC ........................................................ 235/492
See application file for complete search history.

(56) References Cited

U.S. PATENT DOCUMENTS

| | | |
|---|---|---|
| 8,201,323 B2 | 6/2012 | Miller et al. |
| 8,770,479 B1 | 7/2014 | Shoenfeld |
| 10,321,968 B2 * | 6/2019 | Burgess ................. A61B 50/37 |
| 2008/0001760 A1 | 1/2008 | Oh et al. |
| 2008/0139866 A1 * | 6/2008 | Fisher .................... A61B 90/96 |
| | | 588/249 |
| 2008/0316045 A1 | 12/2008 | Sriharto et al. |
| 2012/0212330 A1 | 8/2012 | Halberthal et al. |
| 2012/0305132 A1 * | 12/2012 | Maness ..................... A61J 1/14 |
| | | 141/69 |
| 2013/0237949 A1 | 9/2013 | Miller |
| 2014/0197954 A1 | 7/2014 | Caputo et al. |
| 2014/0374294 A1 * | 12/2014 | Joyce ..................... G16H 20/10 |
| | | 206/363 |
| 2015/0127362 A1 * | 5/2015 | DeBusk .............. G07F 17/0092 |
| | | 705/2 |
| 2017/0286903 A1 | 10/2017 | Elizondo, II |
| 2018/0090228 A1 | 3/2018 | Philippe et al. |

FOREIGN PATENT DOCUMENTS

| | | |
|---|---|---|
| WO | 2014/204958 A1 | 12/2014 |
| WO | 2015/076746 A1 | 5/2015 |

* cited by examiner

DEVICE FOR MONITORING MEDICAMENT DELIVERY DEVICES

CROSS REFERENCE TO RELATED APPLICATIONS

The present application in a continuation of U.S. patent application Ser. No. 15/577,659, filed Nov. 28, 2017 which is a U.S. National Phase Application pursuant to 35 U.S.C. § 371 of International Application No. PCT/EP2016/062976 filed Jun. 8, 2016, which claims priority to European Patent Application No. 15171973.9 filed Jun. 12, 2015. The entire disclosure contents of these applications are herewith incorporated by reference into the present application.

TECHNICAL AREA

The present disclosure relates to a device for monitoring medicament delivery devices and in particular a system where the traceability of medicament delivery devices is enhanced.

BACKGROUND

Monitoring aspects of self-administration is becoming more and more important from several aspects. One aspect is that many physicians would like to have more information regarding how a patient is handling the administration of drugs, especially if the patient is following a treatment scheme. In many cases the physician has to rely on what the patients are telling, which may or may not be actually according to the truth. This gives an uncertainty as to how well the patient is responding to the treatment. For instance, if the patient misses several occasions when a dose was to be administered, or administers doses too unregularly, too close to and/or too far to a previous dose, then this may adversely affect the treatment, which could be misinterpreted that the treatment scheme is not good. In that respect, it might be that the patient does not want to tell the physician that he/she has not followed the scheme and may even discard medicament delivery devices that have not even been used in order to conceal that the treatment scheme has not been followed.

Some solutions to monitor user behaviour have been directed at not having the device as such performing any monitoring or recording when the device is being used but to utilize other equipment that is used in connection with medicament delivery devices. One such equipment is a safety container such as a sharps bin, sharp objects container, medical safety box, biohazard container and the like, that is required when handling medicament delivery devices arranged with injection needles that may cause injuries such as unintentional needle sticks. The user is requested to discard the medicament delivery devices as soon as possible in the safety container The use of a safety container may be utilized for obtaining information regarding the user's behaviour. The use of a safety container instead of monitoring by the device as such is an advantage in that the medicament delivery device needs not be modified in order to be able to monitor, record, store and/or transmit information regarding the use of the medicament delivery device.

One solution incorporating a safety container is disclosed in the document WO 2014/204958. The document discloses an apparatus for obtaining information from used medicament delivery devices before they enter the safety container. According to a favourable embodiment, the apparatus will have a section or compartment before the safety container comprising a sensor that is capable of recording date and time and specifically by creating an image of the medicament delivery device passing the sensor. The sensor is then capable of transmitting the captured information wirelessly to a communications device by different technologies such as RFID, NFC, Bluetooth, etc. Also Ethernet lines or WiFi devices may be used.

The apparatus according to WO 2014/204958 is rather complicated in view of the function and the information obtained. The image creating sensor or camera is an expensive solution for providing a time stamp of the discarding of a used medicament delivery device. It is stated that the image sensor is capable of detecting specific types of waste, but it is very unclear how this may be done or for what purpose. The apparatus has further no blocking elements or the like preventing other objects from being thrown into the safety container.

There are other aspects of the handling of medicament delivery devices that are important and that is an overall traceability not only connected to adherence, but also regarding expiry date of the drug, recall of drug batches, prevention of parallel import as well as recyclability. It would therefore be an advantage if a medicament delivery device has a unique identification element that can be utilized to monitor adherence as well as to in addition trace the medicament delivery device from manufacture to recycling worldwide.

SUMMARY

The aim with the present disclosure is to remedy the drawbacks of the state of the art devices. This aim is obtained by a device comprising the features of the independent patent claim. Preferable embodiments form the subject of the dependent patent claims.

The disclosure relates to a device for monitoring medicament delivery devices. These may comprise a number of different designs and in particular, but not exclusively, devices which are handled outside hospital environments, e.g. at home, and often by the patients themselves. The medicament delivery devices could be inhalers, tablet dispensers and in particular injectors having injection needles and the like which may cause injuries. The word monitoring is to be interpreted as incorporating obtaining and/or collecting specific identification data of a medicament delivery device.

The medicament delivery devices are arranged with information retaining elements comprising information that may be unique to specific medicament delivery devices, whereby each medicament delivery device can be identifiable. According to handling and user instructions, these medicament delivery devices are to be put in a safety container after use.

In the following description the wording safety container will be used and it is to be understood that this wording may comprise any container capable of containing a number of different medical waste products, such as lancets, scalpels, band aids, gauze and many more products that either may cause injury if handled wrongly and/or are bio hazardous, risking of causing transfer of infectious, possibly lethal, diseases, in a safe way so as not to harm people or the environment.

The device comprises an information obtaining mechanism operably arranged to obtain information from medicament delivery devices entered into said safety container. The information regarding the medicament delivery devices is thus obtained by the information obtaining mechanism that can derive various data depending on the type of information retaining elements and the type of data stored on these elements.

According to one solution, the device may be arranged connectable to the safety container. This may be an advantage in order to ascertain that the information obtaining mechanism is within reading distance of the medicament delivery devices that have been thrown into the safety container. As an alternative, the device may be arranged as a stand on which the safety container may be placed. This provides a slim and handy solution where the safety container stands on top of the stand and wherein the stand is arranged with the information obtaining mechanism close to the area where the discarded medicament delivery devices are placed.

Regarding the information retaining elements, they may in a preferable solution comprise wireless technology information tags, and wherein the information obtaining mechanism comprises wireless receiving elements capable of obtaining information wireless from the information tags. One such wireless technology may comprise radio frequency identification; RFID. The advantage with the RFID technology is that a large number of information tags may be read at the same time. Another advantage is that the RFID technology provides the possibility of reading information tags at some distance, especially if ultra-high frequency RFID is used.

According to on feasible solution, the device may preferably further comprise an electronics circuit capable of providing a triggering signal each time the information obtaining mechanism obtains information from a specific medicament delivery device entered into the safety container. The producing of a triggering signal may be the most basic function that the electronics unit may provide when detecting a medicament delivery device. The triggering signal may for example be used for creating a time stamp when the electronics unit has a clock or time counter function, wherein the time may be derived when the signal was triggered, either directly by the clock function or by counting from a known start moment.

The electronics circuit of the device may further comprise storage elements capable of storing the time stamps. In this way the handling history of using and subsequently discarding medicament delivery devices may be stored and then later retrieved from the storage elements. In that respect, the device may further comprise a communication unit, operably arranged to communicate the triggering signals or the time stamps to external information receivers. The handling history may be transferred the patient, relatives or to persons responsible for the treatment of patients, like physicians that have designed individual treatment schemes to patients, wherein this information will provide a record of the compliance or adherence of the patients treatment scheme.

According to a favourable solution, the communication unit may comprise a wireless communication circuit, and wherein the wireless communication circuit is designed to communicate via near range communication technologies, cellular radio communication networks and/or local area networks. With this solution, there are a number of possibilities how the stored information in the device may be transmitted to external information receivers without the use of physical connection by data cables or the like.

In addition to the time stamps, the information retaining elements may contain additional information that is specific to each medicament delivery device and wherein the information obtaining mechanism is capable of deriving the specific information. In this respect, the specific information may be stored in said storage element. Further, the communication unit may be capable of transmitting the specific information to the external information receivers.

According to a further preferable solution, the device may further comprise a weight recording mechanism capable of weighing the medicament delivery devices entered into said safety container. This solution provides the possibility of obtaining further data regarding user handling and user adherence. For instance, regarding user handling, the weight information can be used keeping track of how many medicament delivery devices that have been entered into the safety container. Further, if the specific weight of each medicament delivery device when delivered is known, then the weighing of the discarded medicament delivery device will give an indication if the medicament contained in the delivered medicament delivery device has been administered or not.

Further information that the device may obtain are from additional sensors capable of sampling and analysing body fluids of a patient, wherein the information obtaining element is capable of obtaining the analysed data. The body fluids may for example come from blood samples, saliva, tears from eyes, urine and the like that may readily be taken and analysed. This provides further possibilities of monitoring the progress of the treatment of the patients. In this respect, the sensors may be arranged on the device, integrated in the medicament delivery devices or in external stand alone devices.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which

DETAILED DESCRIPTION

In the following description, the wording smart devices will be used. In this context, smart devices may include electronic devices that are provided with processors that are capable of running computer programs and storage space to store programs as well as data retrieved from different external sources. It is further to be understood that the smart devices are provided with communication systems that are capable of communicating with data networks in order to access different databases. It is to be understood that databases may be accessed via the internet, so called cloud services, and/or databases that are connected directly to and accessed via local area networks. It is further to be understood that the smart devices in this context comprise some sort of human-machine interface for two-way communication. The human-machine interface may comprise displays, keyboards, microphones, loudspeakers, I/O-ports for connection of peripherals. Further the smart devices may be provided with antennas for wireless communication with the networks. Also, the smart devices may be arranged with receiving and transmitting mechanisms capable of communicating with RFID/NFC tags as well as programs capable of establishing and handling the communication with the RFID/NFC tags.

Further, in the following description, the wording medicament delivery device will be used. In this context, medicament delivery devices may include a number of devices capable of delivering certain doses of medicament to a user, such as e.g. injection devices with or without injection needles, inhalers of all kinds, such as powder, aerosol driven, gas, nebulizers having mouth or nasal pieces, but in particular medicament delivery devices that may cause injuries or be harmful if not handled properly, especially after use.

The present disclosure relates to a device for obtaining information from medicament delivery devices that have been discarded, which information can be used for different purposes such as adherence of a prescribed treatment plan of a patient There are a number of different technologies that are applicable but the most favourable technology regarding cost, usability, readability, and attachment possibilities is the Radio Frequency Identification, RFID, technology.

RFID has found its use in many applications where objects can be identified in a simple and fast manner. In many applications, passive RFID tags are used, and in particular as labels that are attached to objects or components that are to be traced. A special type of RFID is a Near Frequency Communication NFC technology that can be applicable in some instances. However, the NFC technology requires that a reader and a tag are close to each other, in the order of 10 cm or less. That will then require that devices arranged with NFC-tags are close to an NFC-reader, which may not be possible in all circumstances. However, if RFID-tags are used, and especially ultra high-frequency tags, then a large number of devices arranged with such tags may be read at the same time and from some distance.

In a preferred embodiment, all medicament delivery devices used are arranged with at least one RFID-tag. The RFID tag is arranged with information that is unique to the specific medicament delivery device. The information may comprise a unique serial number or the like. An external database may then be set up connecting further information to the specific serial numbers such as date of manufacture, batch numbers of components comprised in the medicament delivery device, the weight of the medicament delivery device as delivered to a user without any protecting packaging or other components that should be removed before use, the type of drug contained in the medicament delivery device, batch number of drug, date of manufacture of drug as well as expiry date of the drug, just to mention a few types of information connected to the medicament delivery device.

It is however to be understood that the further information mentioned above that is comprised in the external database may be stored in the RFID tag itself if such a tag is chosen that has a memory capacity that can store the information. The RFID tag is then programmed at the manufacturing of the medicament delivery device with all necessary information regarding both the medicament delivery device as well as the drug.

In order to monitor the behaviour or adherence to a treatment scheme, an RFID-reader is arranged to a safety container. According to instructions, each time a medicament delivery device has been used, it is to be thrown in the safety container. This is registered by the RFID-reader arranged such that it can read RFID-tags inside the safety container.

Figure 1:
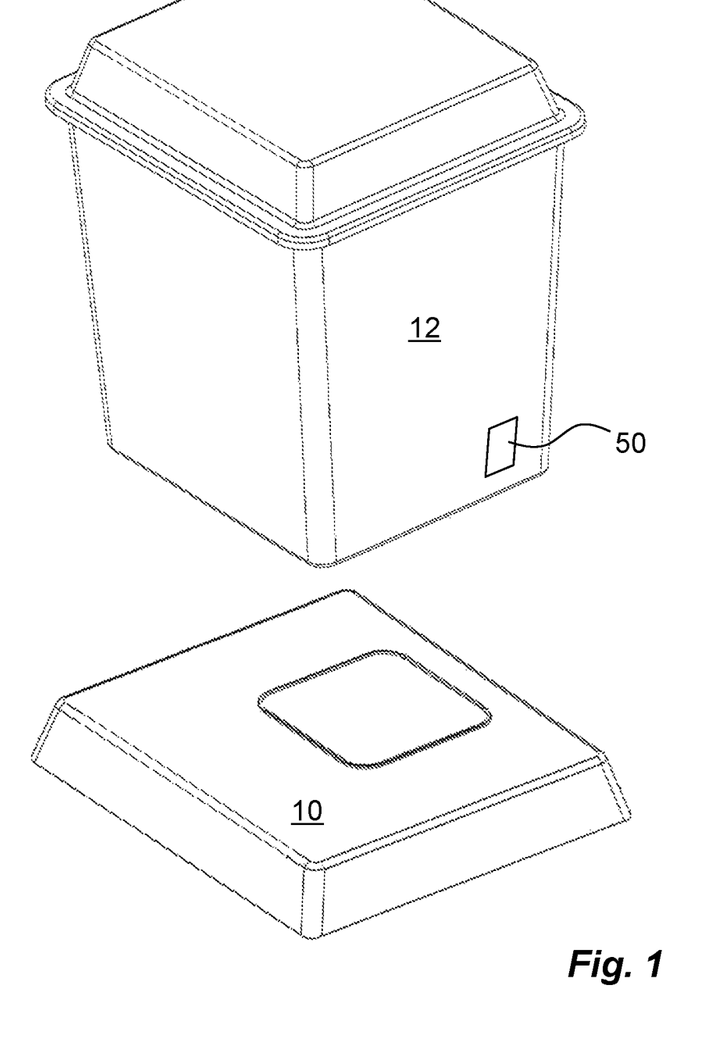
FIG. 1 shows a perspective view of an embodiment of the device together with a safety container.

According to one feasible, non-limiting solution as seen in FIG. 1, it comprises a base 10 or stand on which a safety container such as a sharps bin 12 may be placed on or attached to. The safety container 12 may be any ordinary sharps bin or medical safety box and does not require any specific features or designs. The base 10 may be arranged with a number of features and functions as will be described.

Figure 2:
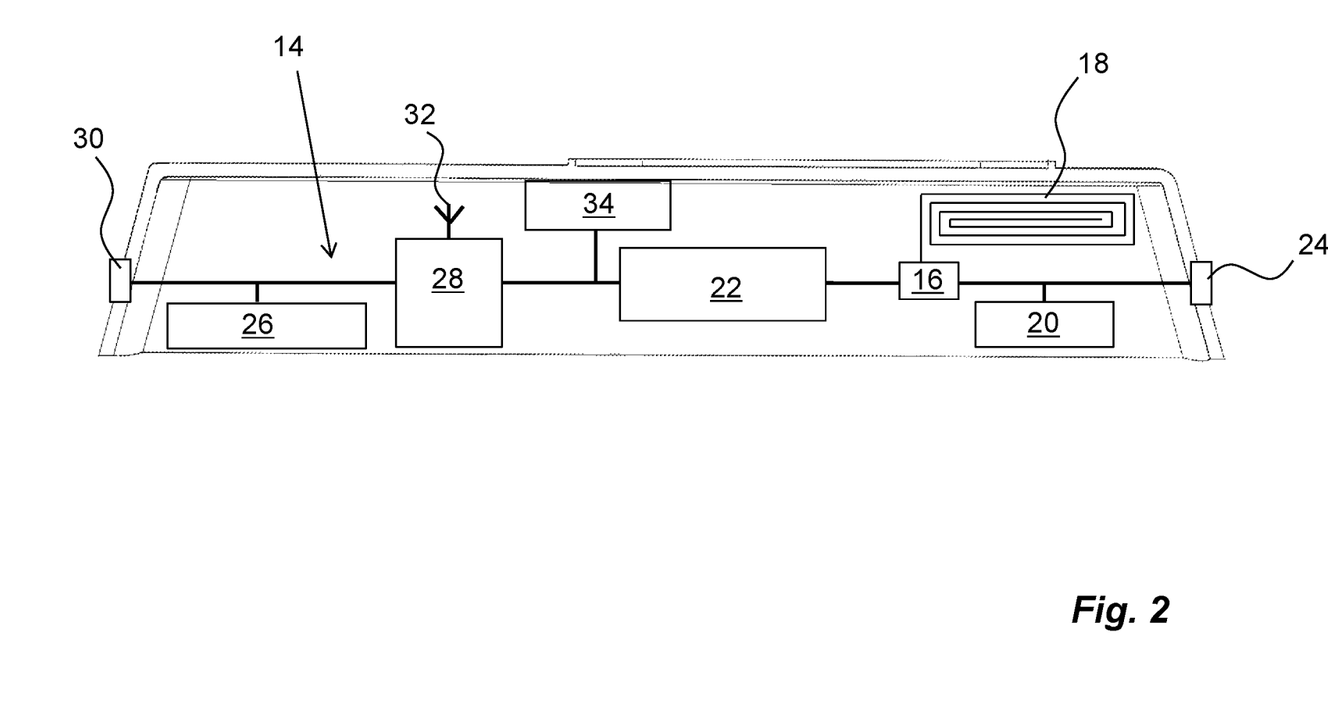
FIG. 2 shows a cross-sectional view of the device of FIG. 1.

An electronics circuit 14 is arranged in the base, FIG. 2. It comprises an RFID reader circuit 16, which in turn comprises an antenna 18 capable of reading the RFID-tags on medicament delivery devices thrown into the safety container 12. It further comprises memory storage elements 20 for storing data retrieved by the RFID reader. Further, a processor 22 is arranged for performing a number of functions based on data program code stored in the memory storage elements. The base could also be arranged with suitable human interface devices 24 such as displays, indication lamps, keyboards, loudspeakers, microphones etc. depending on the desired functions. The electronic circuit is further arranged with a suitable power source 26 for its function, which could be batteries, photovoltaic panels, or power from mains.

The base is further arranged with a communication circuit 28. This may comprise suitable connection elements 30 such as sockets for USB-devices and/or cables, Ethernet-sockets, and the like attachment elements for cables suitable for communication. Also, the communication circuit may be provided with transmitting elements 32 for wireless communication. The wireless communication elements may comprise near range communication technology such as RFID, NFC or the like, as well as Bluetooth, Ant, Zigbee, just to mention a few.

However, the wireless communication elements may preferably comprise cellular radio communication networks, e.g. GSM, 3G, 4G, etc. and/or wireless local area networks, which networks can provide access for the base to the internet and thus to a large number of external data storage sources, data handling centres, etc.

One of the functions or features of the base could be that the electronics circuit may have a timer function capable of providing a time stamp of when a medicament delivery device has entered the safety container and been identified by the RFID-reader. The time stamp may then be stored in the memory of the electronics circuit. One or several stored time stamps may then be retrieved by appropriate data retrieving technologies. One such could be a portable memory connected to the I/O interface of the base. The portable memory may comprise a USB memory which may be attached to appropriate receptacles for retrieving the stored time stamps.

The USB memory may thereafter be connected to a computer or other smart device that can process the data of the time stamps. In that manner, the patient's usage behaviour over time may be monitored. The usage behaviour may be compared to a prescribed treatment scheme that the patient has received from his/her physician or other medically skilled person, whereby the adherence of the patient will be derived. Any deficiencies in the adherence can then be addressed by the physician of the patient.

Also or instead, a communication cable such as a USB cable may be connected, which cable may be attached to a computer or a smart device with its other end, whereby stored time stamps are transmitted via the cable and handled in the same manner as above. Also, or instead, the retrieved data, either by a portable memory or by cable, may be transmitted by the computer or smart device to remote information storage sources, e.g. on the internet, by using the communication capabilities of the computer or smart device.

Thereby, the user or patient may use his/her own computer or smart device for retrieving saved time stamps and to use appropriate available communication networks for transmitting the retrieved data to a dedicated information source, from which a physician or medically skilled person may obtain and process the data. The physician or skilled person may then use the communication networks transmit information to the computer or smart device of the user regarding the adherence of the patient and to alert or instruct the patient depending on the results.

However, if the communication elements are arranged in the base as such, then the base may communicate directly with external data storage sources, data handling centres etc. via the communication networks. Time stamps may then either be stored locally and transmitted at specific intervals or may be transmitted directly without storage.

If the RFID-tags are provided with further information that is stored therein, then this additional information may be transmitted together with the time stamps to external databases and stored there. This information may then be used by a number of functions for handling the medicament delivery devices. For instance, the information may be used as mentioned in connection with recycling operations, as well as other processes where information regarding the device is necessary.

In addition to information regarding used medicament delivery devices the user may provide further information that is directly patient-oriented. One area that is growing steadily is patient reported outcome or PRO. The PRO's are methods or questionnaires where responses of treatment schemes of clinical trials are obtained directly from the user or patient. Commonly assessed features may comprise symptoms and other aspects of well-beings, overall functioning of patient, health status, general health perceptions, quality of life, health related quality of life, ratings of treatment etc. Such information may be entered by the patient or user via the human interface of the base and then transmitted to suitable databases for further handling of the information. The PRO information may as an alternative be entered by the patient via his/her computer or smart device when handling data from the electronics circuit of the base.

As a further alternative, the human interface may comprise a voice recognising function, wherein the patient or user may enter PRO information by speech. There could in that regard be an interaction wherein the electronics could pose questions via the human interface, which are answered by the patient. The recorded answers could then be transmitted to suitable databases for further handling. Regarding the voice recognising function, it may even be advanced enough to recognise voices from specific persons. This may for example provide the possibility for several users or patients to use the same stand for entering PRO information, wherein the electronics is able to connect recorded answers with specific persons. Also, if several patients are using the safety container for disposing of used medicament delivery devices, the electronics of the base may be activated such that is poses a question who is disposing the medicament delivery device. The electronics may then be able to register specific persons and connect them to the disposed medicament delivery devices by recognising the voice of the answering person.

Regarding detection and registration of specific persons using the same safety container it is of course possible to utilize other identification mechanisms such as biometric methods, i.e. fingerprint detection, eye detection etc. The electronic circuit is then arranged with appropriate sensors and biometric readers that are capable of identifying individual users. Further, the human interface may be arranged with a keyboard or key pad as mentioned above, wherein a user enters a personal code each time a medicament delivery device is discarded in the safety container.

The electronics circuit may further be arranged with a function of counting and storing the number of medicament delivery devices that are collected in the safety container. The I/O devices of the base may then alert a user when a predetermined number of medicament delivery devices have been discarded in the safety container, indicating that the safety container is full and needs to be replaced with a new safety container. The number of medicament delivery devices discarded may also be used for initiating a refill of the prescription of drugs. For instance a certain number of used and discarded devices may trigger a message to the physician or the pharmacy of the patient that the prescription needs to be renewed.

In addition to the time stamps and the number of medicament delivery devices that the base may collect, further information stored in the RFID tags may be collected and/or used.

In that respect, the base may comprise a weight measuring device comprising weight sensors 34 connected to the electronics circuit. The processor is then capable of calculating the weight of individual medicament delivery devices based on the information from the weight measuring device as well as the total weight of the medicament delivery devices inside the safety container. This information may on the one hand be used to alert when a predetermined total weight has been reached, indicating a full safety container, in turn leading to an alert.

On the other hand, the information may be used in detecting if the medicament delivery device has been used or not, if the electronics circuit has been provided with information regarding the weight of medicament delivery devices that the user has been prescribed. The weight information could be derived on a specific device basis since each medicament delivery device is unique if it has been provided with an RFID-tag. The specific medicament delivery could then have been weighed at the assembly plant, which weight could be stored at an information storage location accessible to the communication circuit of the base or stored in the RFID-tag.

When detecting and recognizing a discarded medicament delivery device and recording its weight, the electronics circuit could then be programmed to retrieve weight data from either the external information storage location or from the RFID-tag and compare the two weights. If the weight differs within a predetermined range, this is an indication that the medicament delivery device has been used. On the other hand, if the difference is very small or none, this is an indication that the medicament delivery device has been discarded unused. If on the other hand the recorded weight is outside both an unused and a used medicament delivery device and/or no reading can be obtained when sensing a weight, this is an indication that unidentified material has been disposed, which may not be allowed.

The weight information may then be transmitted to a physician of the user, alerting that the user has not complied with the treatment scheme. In this context it is of course possible that the weight information is sent to an external data processing location where the retrieval of the initial weight of the medicament delivery device is retrieved and compared to the weight transmitted by the base. Regarding transmission of data to a data processing location and to a physician or health care giver, it is of course possible to transmit data the other way, i.e. from a physician to the electronics circuit. The data may then be presented to the user of the safety device. For instance, a physician may want to do changes in the treatment scheme depending on the results obtained from the data transmitted from the electronics circuit of the stand and this change can then be presented via the human interface, which may be audibly, a voice message or visually via a written message. If more people are using the safety container, messages directed to specific persons may be accessible via the identification mechanism mentioned above.

Even though a solution with a stand, on which a safety container is placed, is advantageous because a weight function can be used, it is of course possible to have the device releasably connectable on any surface of the safety container such as on the side or on top of the container. Because of the reading range of the RFID reader, the device may not even be directly connected to the safety container, but may be placed at some distance.

Figure 3:
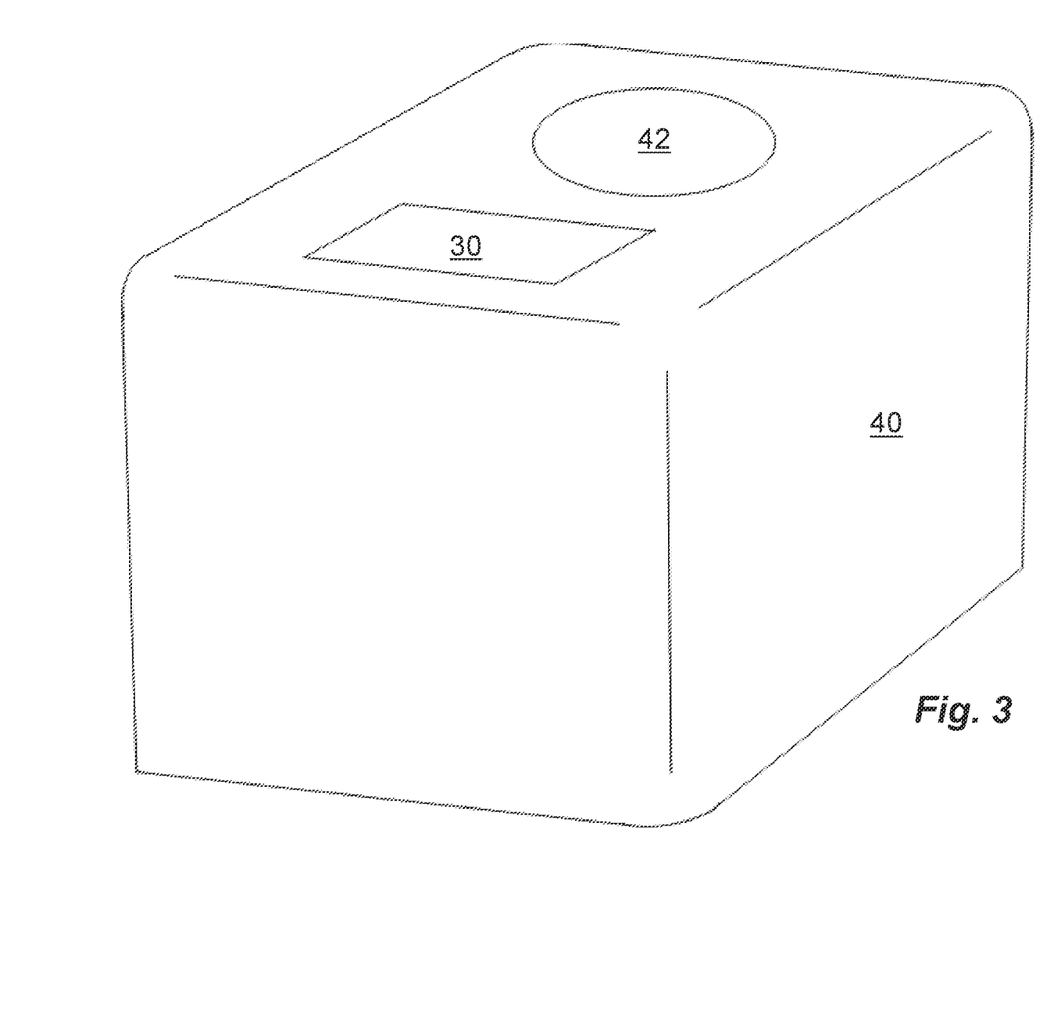
FIG. 3 shows an enclosure for the device of FIG. 1 such that the device is hidden from view.

As another alternative, the stand and the safety container may be placed in an enclosure or have a cover 40, FIG. 3, such that the safety container is hidden from view. This may be a feature appreciated by many users wanting a more discrete appearance than the often bright red and yellow safety containers. With a discrete enclosure or cover 40 the safety container may be placed in for example the kitchen without being conspicuous. The cover is then preferably arranged with an opening or passage 42 so that the hidden safety container may be accessed without having to remove the cover.

Figure 4:
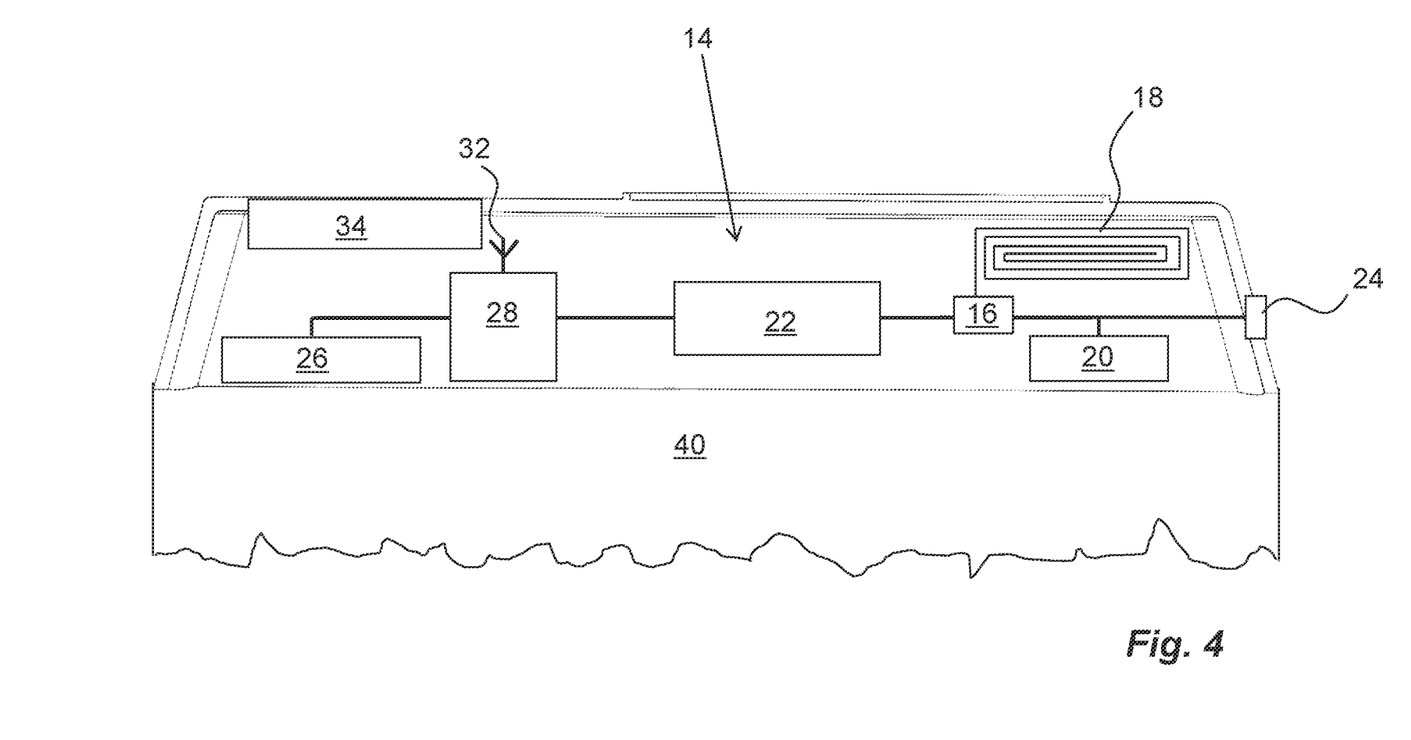
FIG. 4 is a perspective view of the enclosure of FIG. 3 containing electronics associated with the device.

As a further alternative, the electronics that in the previous embodiment was placed in the stand below the safety container may now instead be placed in the cover, and preferably in the upper part of the cover as seen in FIG. 4. This enables the human interface 34 to be placed so that it is easily accessible for a user, both for displaying information as well as entering information. The cover may then be arranged with an ordinary bottom or without any bottom. As with the previous embodiment, this solution may comprise all information and communication features as seen in FIG. 4, enabling communication to and from the cover. One advantage with this solution is that, if NFC or RFID readers are used, the direction of the beams from the readers may be directed inwards/downwards towards the safety container, reducing the spreading of radiation in the room or space that the device is placed.

Further, the safety container as such may be arranged with an RFID-tag 50 that can be read by the RFID-reader of the base. When a new safety container is placed on the base, this is registered by the electronics of the base, and the information regarding the safety container may be transmitted to external databases via the communications circuit. Further, the RFID-tags of the safety container may be used in connection with the user handing in a full safety container to enterprises that are authorised to handle safety containers, such as e.g. pharmacies, for destruction. The safety containers may then be identified, enabling traceability of both the individual safety containers as well as individual medicament delivery devices stored therein. Further, the RFID-tag of each specific medicament delivery device may comprise information regarding a complete list of materials contained in the medicament delivery device, which information may be used to form a complete list of disposed material, which list may be used for enabling or facilitating recycling of material.

By using the unique information carriers like RFID-tags, it is possible to trace and to keep track of medicament delivery devices in a controlled manner from manufacture to destruction of the devices. In order to be able to trace and track the medicament delivery devices some sort of identification mechanism has to be utilized.

Since the medicament delivery device is arranged with an RFID-tag, this feature may be used in a number of situations and for a number of functions. For instance, the medicament delivery device may be arranged with an RFID-tag at the manufacturing stage. During the manufacturing stage, the RFID-tag is programmed by appropriate equipment capable of writing information to the RFID-tag. The RFID-tag may further comprise additional sensors such as temperature sensors, wherein the temperature sensors may be used for logging the temperatures that the medicament delivery device has been exposed to. The temperature log may then be used for controlling and/or alerting if the medicament delivery device has been exposed to excess temperatures, which may be important to drugs whose performance is dependent on the right temperatures.

The RFID-tag of the medicament delivery device may in addition be able to communicate with additional sensors of the medicament delivery device such as clocks, switches, sensors, etc. In this respect, the medicament delivery device may be arranged with sensors that are capable of obtaining samples from the body of a patient, such as blood, saliva, tears or urine, and may analyse the sample in order to provide information of the health status of the patient, sometimes referred to as lab on a chip or LOC or biosensors. This information may then either be stored in the RFID-tag or be transmitted to external information centres when the medicament delivery device is discarded in the safety container. It is to be understood that the LOC may be arranged on another device than the medicament delivery device. This device may then be arranged with an RFID-tag that may be read by the RFID-reader of the stand. Some LOC or sensors may be powered by electromagnetic induction from magnetic fields produced near the reader. Some types collect energy from the interrogating radio waves and act as a passive transponder. Other types have a local power source such as a battery. In that respect, regarding electromagnetic induction, the RFID-readers antenna may be sufficient to power the LOC's or biosensors. As an alternative, if the LOC's or biosensors require more power, but do not have local power sources, additional antennas may be built into the device. The power supplied may be used for "wakening" the LOC's or biosensors and then for performing the analyses.

Since each medicament delivery device is arranged with a unique serial number, it is easy to trace each specific medicament delivery device in the logistics chain from the manufacturing/assembly plant to the user, by providing reading of the RFID-tags along the logistics chain and comparison with the data provided from the external databases, preferably cloud-based. It is therefore very easy to detect and identify any counterfeit products and/or products that have been parallel imported.

Even though the wording medicament delivery device has been used above, it is to be understood that this wording in the present context may comprise a number of medical waste products, such as lancets, scalpels, band aids, gauze and many more products that either may cause injury if handled wrongly and/or are bio hazardous, risking of causing transfer of infectious, possibly lethal, diseases, which products may be arranged with unique information retaining elements as described above.

It is to be understood that the embodiments described above and shown in the drawings are to be regarded only as non-limiting examples of the disclosure and that they may be modified in different ways within the scope of the patent claims.

The invention claimed is:

1. A system for disposing of used medical devices and medical wastes comprising:
   a disposable sharps container designed to (a) accept used medical devices or medical wastes that are thrown directly into the sharps container by a user such that a biohazardous transfer of diseases or accidental needle sticks is prevented once the used medical devices or the medical wastes are directly deposited in the sharps container and (b) prevent the deposited used medical devices or medical wastes from being removed from the sharps container; and
   an information obtaining mechanism that is directly connected to the sharps container, where the information obtaining mechanism comprises an information reader that reads information wirelessly from information tags that are attached to the deposited medical wastes or to used medical devices when entering or contained within the sharps container,
   wherein the information obtaining mechanism is configured so that both the sharps container and the used medical devices or medical wastes deposited into the sharps container can be individually identified and traced as the sharps container is transferred from a user of the sharps container to enterprises that are authorized to safely destroy the sharps container,
   wherein the information obtained from the reader is transmitted to an external information receiver that is separate and distinct from the information obtaining mechanism,
   wherein the transmitted information obtained from the reader comprises a list of the used medical devices or medical wastes that are thrown directly into the sharps container, and
   wherein disposal of the sharps container results in simultaneous disposable of the medical devices or medical wastes, the information reader and the information tags.

2. The system according to claim 1, wherein the information obtaining mechanism is directly connected to a stand that is configured to accept, hold or support the sharps container.

3. The system according to claim 1, wherein the information retaining elements comprise wireless technology information tags, and wherein the reader comprises wireless receiving elements capable of obtaining information wirelessly from the information tags.

4. The system according to claim 3, wherein the information tags comprise radio frequency identification (RFID) elements.

5. The system according to claim 1, wherein the information obtaining mechanism further comprises an electronics circuit that provides a triggering signal each time the reader obtains information from a deposited medical waste or used medical device within the sharps container.

6. The system according to claim 5, wherein the electronics circuit creates a time stamp when the triggering signal is provided.

7. The system according to claim 6, wherein the electronics circuit further comprises storage elements that store the time stamps and information received by the reader.

8. The system according to claim 1, wherein the electronics circuit comprises a communication unit that communicates the triggering signals or the time stamps to the external information receiver.

9. The system according to claim 1, wherein the information obtaining mechanism further comprises a weight recording mechanism that determines a weight for deposited medical waste or used medical device within the sharps container.

10. The system according to claim 9, wherein the weight determination is made using weight information contained in the information retaining elements and that is read by the reader.

11. The system according to claim 9, wherein the weight recording mechanism further determines when the sharps container is full.

12. The system according to claim 9, wherein the weight recording mechanism further determines a quantity of medicament in the deposited used medical devices such that a determination of delivered medicament is obtained and transmitted to the external information receiver.

13. The system according to claim 1 further comprising a human interface that has a voice recognition function such that the user can enter a patient reported outcome.

14. The system according to claim 1 further comprising a biometric identification mechanism that can identify the user using a fingerprint sensor or eye detection sensor.

15. A method for monitoring and tracing used medical devices comprising:
    providing a disposable sharps container designed to (1) accept used medical devices that are thrown directly into the sharps container by a user such that a biohazardous transfer of diseases or accidental needle sticks is prevented once the used medical devices are deposited in the sharps container and (2) prevent the deposited used medical devices from being removed from the sharps container;
    providing an information obtaining mechanism that is directly connected to the sharps container, where the information obtaining mechanism comprises an information reader that reads information wirelessly from information tags that are attached to the deposited used medical devices when entering or contained within the sharps container;
    reading the information from the information retaining elements;
    transmitting the information to an external information receiver that is separate and distinct from the information obtaining mechanism; and
    transferring the sharps container to enterprises that are authorized to safely destroy the sharps container, where the information obtaining mechanism must be transferred with the sharps container and is configured so that both the sharps container and the used medical devices deposited into the sharps container can be individually identified and traced as the sharps container is transferred such that the information obtaining mechanism is destroyed along with the sharps container and the used medical devices.

16. The method of claim 15 further comprises weighing the deposited used medical devices.

17. The method of claim 16 further comprises determining if a predetermined weight of the sharps container has been reached indicating that the sharps container is full.

18. The method of claim 15 further comprises generating a time stamp when a used medical device is deposited into the sharps container.

19. The method of claim 16 further comprises determining a quantity of medicament in the deposited used medical devices such that a determination of delivered medicament is obtained and transmitted to the external information receiver.

20. The system according to claim 15 further comprises providing a triggering signal each time the information obtaining mechanism obtains information a deposited used medical device.

\* \* \* \* \*